(12) United States Patent
Kobayashi et al.

(10) Patent No.: US 8,865,425 B2
(45) Date of Patent: *Oct. 21, 2014

(54) REAGENT AND REAGENT KIT FOR MEASUREMENT OF FDP, AND MEASUREMENT METHOD

(71) Applicant: Sysmex Corporation, Kobe (JP)

(72) Inventors: Katsushi Kobayashi, Kobe (JP);
Masumi Murakami, Kobe (JP);
Mayumi Sugimoto, Kobe (JP)

(73) Assignee: Sysmex Corporation, Hyogo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/753,179

(22) Filed: Jan. 29, 2013

(65) Prior Publication Data

US 2013/0143243 A1 Jun. 6, 2013

Related U.S. Application Data

(63) Continuation of application No. PCT/JP2011/067326, filed on Jul. 28, 2011.

(30) Foreign Application Priority Data

Jul. 30, 2010 (JP) .................................. 2010-172279

(51) Int. Cl.
| | | |
|---|---|---|
| G01N 33/546 | (2006.01) | |
| G01N 33/68 | (2006.01) | |
| G01N 33/86 | (2006.01) | |
| C12Q 1/56 | (2006.01) | |
| G01N 33/58 | (2006.01) | |
| C07K 16/36 | (2006.01) | |
| C07K 16/28 | (2006.01) | |
| C07K 14/75 | (2006.01) | |
| G01N 33/577 | (2006.01) | |

(52) U.S. Cl.
CPC ...... *C07K 16/2803* (2013.01); *G01N 2800/102* (2013.01); *G01N 33/6893* (2013.01); *G01N 2333/75* (2013.01); *G01N 33/586* (2013.01); *C07K 16/36* (2013.01); *G01N 33/86* (2013.01); *G01N 2800/324* (2013.01); *G01N 2800/226* (2013.01); *G01N 2800/224* (2013.01); *C07K 14/75* (2013.01); *G01N 33/577* (2013.01)
USPC ............ 435/13; 436/534; 436/501; 435/355; 530/388.25

(58) Field of Classification Search
None
See application file for complete search history.

(56) References Cited

U.S. PATENT DOCUMENTS

| | | | | |
|---|---|---|---|---|
| 4,208,479 A | * | 6/1980 | Zuk et al. ........................ | 435/7.9 |
| 4,758,524 A | | 7/1988 | Bundesen et al. | |
| 5,091,512 A | * | 2/1992 | Gargan et al. ................. | 436/518 |
| 5,452,359 A | * | 9/1995 | Inanaga et al. ................ | 381/310 |
| 5,821,068 A | * | 10/1998 | Soe et al. ...................... | 435/7.21 |
| 2013/0011869 A1 | * | 1/2013 | Nagahama et al. .......... | 435/7.92 |

FOREIGN PATENT DOCUMENTS

| | | |
|---|---|---|
| EP | 1 085 088 A1 | 3/2001 |
| JP | 59-183696 A | 10/1984 |
| JP | 5-38906 B2 | 6/1993 |
| JP | 7-46104 B2 | 5/1995 |
| JP | 2000-193663 A | 7/2000 |
| JP | 2001-354700 A | 12/2001 |
| JP | 2002-372536 A | 12/2002 |
| JP | 3472138 B2 | 12/2003 |
| JP | 2006-105633 A | 4/2006 |

OTHER PUBLICATIONS

Gaffney, P. J., Breakdown products of fibrin and fibrinogen: molecular mechanisms and clinical implications., J. Clin. Pathol., 33(14), (1980), p. 10-17.*

* cited by examiner

*Primary Examiner* — Christine Foster
*Assistant Examiner* — Ellen J Marcsisin
(74) *Attorney, Agent, or Firm* — Sughrue Mion, PLLC

(57) ABSTRACT

The present invention relates to a reagent for the measurement of FDP comprising a carrier sensitized with at least two monoclonal antibodies selected from three monoclonal antibodies having different reactivity towards FDP. The present invention also relates to a reagent kit comprising the reagent and a method for measurement of FDP using the reagent or reagent kit.

12 Claims, 2 Drawing Sheets

REAGENT AND REAGENT KIT FOR MEASUREMENT OF FDP, AND MEASUREMENT METHOD

CROSS-REFERENCE TO RELATED APPLICATION

This application is a continuation of International Application PCT/JP2011/067326 filed on Jul. 28, 2011, which claims benefit of Japanese patent application JP 2010-172279 filed on Jul. 30, 2010, both of which are incorporated herein by reference in their entireties.

BACKGROUND OF THE INVENTION

The present invention relates to a reagent and reagent kit for the measurement of fibrinogen and fibrin degradation products (FDP), and to a method for measurement of FDP.

When thrombi (stabilized fibrin) are formed in blood vessels or tissues due to hemostasis or other pathogenic causes, fibrinolysis is developed in vivo to remove the thrombi. The fibrinolysis for lysing thrombi is called secondary fibrinolysis in which fibrin in thrombi is degraded by enzymatic actions such as plasmin to produce fibrin degradation products (FbnDP: secondary fibrinolysis products) in blood. On the other hand, there is another fibrinolysis in vivo, called primary fibrinolysis, which is developed without association with formation of thrombi. During primary fibrinolysis, fibrinogen is degraded by enzymatic actions such as plasmin to produce fibrinogen degradation products (FbgDP: primary fibrinolysis products) in blood. These degradation products of fibrin and fibrinogen are collectively called as FDP (fibrinogen and fibrin degradation products).

The presence of FDP in blood can be an index for predicting in vivo hyperfibrinolysis. Due to this, the measurement of FDP in blood is used for diagnoses of diseases related to thrombi, cardiovascular disorders, hyperfibrinolysis, abnormal hemorrhage and the like or disseminated intravascular coagulation (DIC). Particularly, it is required to measure total FDP amount regardless of the type of FDP in order to classify pathological conditions of DIC.

Immunological approach has been conventionally applied for reagents for the measurement of blood FDP, and reagents utilizing turbidimetric immunoassay are commercially available, for example. Such reagents for the measurement of FDP include reagents using polyclonal antibodies such as anti-human fibrinogen antibodies. However, when FDP are measured with such reagents, the measured value of FDP may be falsely high unless a specimen to be measured is a biological sample of which fibrinogen has been deprived such as serum. However, the preparation of serum is complicated. In addition, because plasma is used as specimens for blood coagulation tests such as PT (prothrombin time), APTT (activated partial thromboplastin time), Fbg (fibrinogen concentration) and the like, reagents for the measurement of plasma FDP using monoclonal antibodies are clinically preferred in which plasma can be used as specimens (see Japanese Patent Publication Nos. Hei 5 (1993)-38906 and Hei 7 (1995)-46104, Japanese Patent No. 3472138 and Japanese Unexamined Patent Publication Nos. 2001-354700 and 2002-372536).

SUMMARY OF THE INVENTION

Reagents for the measurement of FDP using serum react equally with primary and secondary fibrinolysis products. However, it is observed that monoclonal antibodies used in conventional reagents for the measurement of plasma FDP have different reactivity towards primary and secondary fibrinolysis products. Namely, the conventional reagents for the measurement of plasma FDP tend to have higher reactivity towards secondary fibrinolysis products than towards primary fibrinolysis products.

In general, fibrinogen is not degraded under physiological conditions. Accordingly, secondary fibrinolysis products account for a major portion of FDP, making the above difference in reactivity less problem under normal measurements. However, biological samples obtained from patients suffering from DIC or acute promyelocytic leukemia, who are in such a condition that blood plasmin is hyperactivated to enhance primary fibrinolysis, contain primary fibrinolysis products. Thus, the total FDP amount in subjects with the condition of hyperfibrinolysis may not be measured accurately with conventional reagents for the measurement of plasma FDP having lower reactivity towards primary fibrinolysis products.

An object of the present invention is to provide a reagent and reagent kit which react equally with both primary and secondary fibrinolysis products to allow accurate measurement of FDP in subjects with the condition of hyperfibrinolysis. A further object of the present invention is to provide methods for measurement of FDP using the reagent and the reagent kit.

The present inventors have carried out extensive studies and found that when a reagent containing a suspension of carrier particles sensitized with at least two monoclonal antibodies having different reactivity towards FDP is used, the carrier particles react equally with primary and secondary fibrinolysis products in biological samples, thereby completing the present invention.

Thus, the present invention provides a reagent for the measurement of FDP comprising a carrier sensitized with at least two monoclonal antibodies which have different reactivity towards FDP and are selected from:

a first monoclonal antibody which does not react with the fragment D but reacts with the fragments XDP, DD/E, DD, X and Y;

a second monoclonal antibody which does not react with the fragments X and D but reacts with the fragments XDP, DD/E, DD and Y; and a third monoclonal antibody which does not react with the fragment D but reacts with the fragments XDP, DD/E, DD, X and Y and has different reactivity towards FDP from that of the first monoclonal antibody.

The present invention also provides a reagent kit for the measurement of FDP comprising a first reagent containing a buffer and a second reagent containing a carrier sensitized with the at least two monoclonal antibodies which have different reactivity towards FDP described above.

The present invention further provides a method for measurement of FDP comprising the steps of:

mixing a biological sample with a suspension of carrier particles sensitized with the at least two monoclonal antibodies which have different reactivity towards FDP; and measuring a degree of aggregation of the carrier particles resulting from antigen-antibody reaction.

The reagent and reagent kit for the measurement of FDP and the method for measurement of FDP of the present invention allow highly accurate measurement of FDP even in biological samples containing primary fibrinolysis products which have been difficult to be accurately measured with conventional reagents for the measurement of FDP.

In addition, because the reagent and reagent kit for the measurement of FDP and the method for measurement of FDP of the present invention allow equal reactivity towards primary and secondary fibrinolysis products, both serum and plasma can be used as specimens.

DETAILED DESCRIPTION OF THE EMBODIMENTS

Figure 1:
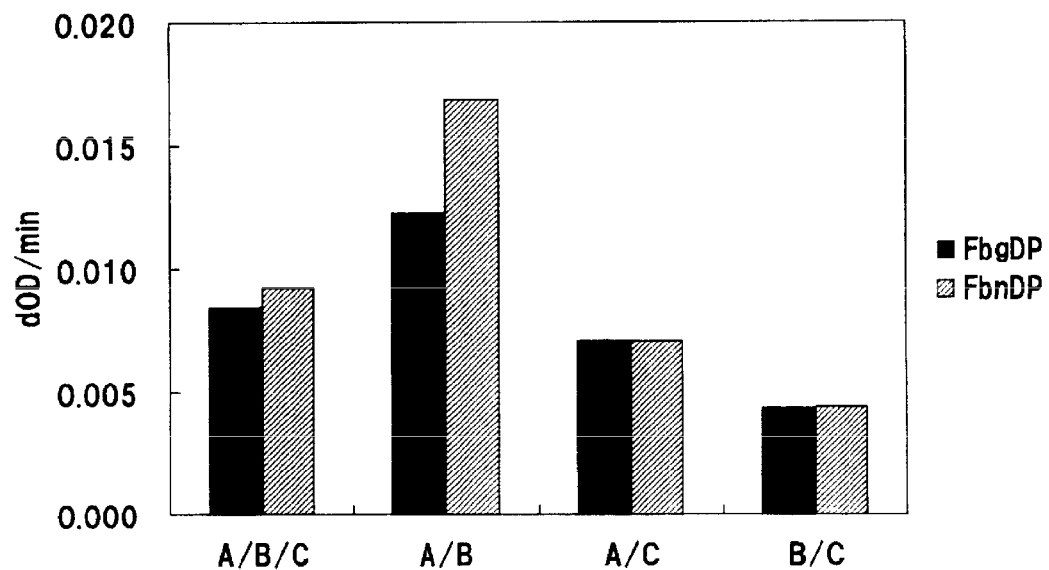
FIG. 1 is a graph showing reactivity of the reagent for the measurement of FDP of the present invention towards primary and secondary fibrinolysis products.

As used herein, the term "FDP" means both fibrin degradation products and fibrinogen degradation products.

As used herein, the term "fibrin degradation products" is also referred to as secondary fibrinolysis products and corresponds to the group of proteins produced by degradation of stabilized fibrin, which is a polymer formed after coagulation of fibrinogen in blood due to enzymatic actions of thrombin and the like, with enzymes such as plasmin and the like. The fibrin degradation products include the fragment DD, the fragment DD/E, the fragment XDP and the like. The fragment XDP includes polymers of the fragment DD/E, e.g., the fragment DXD/YY which is a trimer of the fragment DD/E; the fragment YXY/DXXD which is a pentamer of the fragment DD/E; and the fragment DXXD/YXXY which is a heptamer of the fragment DD/E. In the art, the fragment XDP is also referred to as the D dimer.

As used herein, the term "fibrinogen degradation products" is also referred to as primary fibrinolysis products and corresponds to a group of proteins produced by degradation of fibrinogen in blood with enzymes such as plasmin and the like. The fibrinogen degradation products include the fragment X, the fragment Y, the fragment D and the fragment E.

As used herein, the "reactivity towards FDP" is defined according to the type of FDP which specifically reacts with an anti-FDP monoclonal antibody or according to the degree of aggregation resulting from antigen-antibody reaction between a carrier sensitized with an anti-FDP monoclonal antibody and FDP.

Thus, when an anti-FDP monoclonal antibody specifically reacts with a FDP which is of a different type to the type of FDP reacting with another anti-FDP monoclonal antibody, these antibodies are determined to have different reactivity towards FDP. When two anti-FDP antibodies react with the same type of FDP and there is a significant difference in the degree of aggregation on FDP measurements respectively using carriers sensitized with the respective anti-FDP monoclonal antibodies, it is also determined that these antibodies have different reactivity towards FDP.

The monoclonal antibodies used for the reagent for the measurements of FDP of the present invention (hereinafter also referred to as the present reagent) are at least two monoclonal antibodies having different reactivity towards FDP. Such monoclonal antibodies are preferably at least two selected from the following first, second and third monoclonal antibodies.

The first monoclonal antibody is an antibody which does not react with the fragment D but reacts with the fragments XDP, DD/E, DD, X and Y.

The second monoclonal antibody is an antibody which does not react with the fragments X and D but reacts with the fragments XDP, DD/E, DD and Y.

The third monoclonal antibody is an antibody which does not react with the fragment D but reacts with the fragments XDP, DD/E, DD, X and Y and has different reactivity towards FDP from that of the first monoclonal antibody.

The combinations of the monoclonal antibodies comprised in the present reagent include, for example, "the first and second monoclonal antibodies", "the first and third monoclonal antibodies", "the second and third monoclonal antibodies" and "the first, second and third monoclonal antibodies".

The first, second and third monoclonal antibodies may be any antibodies derived from mammals such as mouse, rat, hamster, rabbit, goat, horse and the like, among which mouse is preferred. The isotype of the antibodies may be any of IgG, IgM, IgE, IgA and the like. The antibodies include fragments and derivatives thereof, which may be exemplified by Fab fragments, F(ab')2 fragments and the like.

The first, second and third monoclonal antibodies can be obtained by immunological procedures known in the art. Namely, the monoclonal antibodies can be obtained by immunizing an animal with antigens, FDP (primary and/or secondary fibrinolysis products), and an adjuvant optionally mixed therewith, fusing B lymphocytes obtained from the animal with suitable myeloma cells to obtain hybridomas and purifying the antibodies from a culture supernatant of the hybridomas.

More specifically, the first, second and third monoclonal antibodies used for the present reagent can be obtained by the following method.

(Preparation of Antigens)

The antigens, FDP, can be obtained by reacting an enzyme capable of degrading fibrin and fibrinogen such as plasmin with fibrin and fibrinogen. The fibrin and fibrinogen, which are starting materials for FDP, are commercially available. Fibrin may also be obtained by reacting fibrinogen with thrombin, factor XIII and a calcium salt.

(Immunization)

The thus obtained antigens may be optionally mixed with an adjuvant and are dissolved or suspended in a suitable buffer to prepare an antigen solution, which can be then used for immunization of an animal. The concentration of the antigens in the antigen solution is preferably around 50 to 500 µg/ml. When the antigens have low immunogenicity, the antigens may be optionally linked to a carrier protein such as albumin, keyhole-limpet hemocyanin.

The adjuvant may be any adjuvant known in the art, which may include, for example, Freund's complete adjuvant (FCA), Freund's incomplete adjuvant (FIA), Ribi (MPL), Ribi (TDM), Ribi (MPL+TDM), *Bordetella pertussis* vaccine, muramyl dipeptide (MDP), aluminium adjuvant (ALUM) and combinations thereof. The particularly preferable combination is to use FCA for priming and FIA or Ribi adjuvants for boosting.

The animal to be immunized may be any of mouse, rat, hamster, horse, goat, rabbit and the like, among which mouse is preferred and BALB/c mouse is more preferred.

The method for immunization can be appropriately selected according to the type of antigens used or the presence or absence of an adjuvant. When a mouse is immunized, for example, the mouse is primed with 0.05 to 1 ml of an antigen solution mixed with an adjuvant (containing 10 to 200 µg of antigens) by an intraperitoneal, subcutaneous, intramuscular or tail vein injection followed by 1 to 4 boost immunizations at about every 4 to 21 days from the prime immunization and a final immunization at about 1 to 4 weeks thereafter. Immunization may be carried out with intraperitoneal injections of a high amount of antigen without an adjuvant in the antigen solution. Antibody titer is measured after 5 to 10 days of the boost immunization(s) by collecting blood. The antibody titer can be measured according to known methods in the art such as the antibody titer assay described hereinbelow. The spleen is recovered from the immunized animal after about 3 to 5 days of the final immunization, from which antibody producing cells can be obtained after separation of spleen cells.

(Preparation of Monoclonal Antibodies)

The monoclonal antibodies can be prepared according to any methods known in the art, for example a method described in Kohler and Milstein, Nature, 256, 495-497 (1975).

Myeloma cells which may be used are the cells derived from any mammals such as mouse, rat, human and the like including mouse myeloma cell lines P3X63-Ag8, P3X63-Ag8-U1, P3NS1-Ag4, SP2/o-Ag14, P3X63-Ag8.653 and the like. When the myeloma cells used for fusion are those producing immunoglobulin light chains, the immunoglobulin heavy chains produced by the antibody producing cells may randomly bind to these light chains. Due to this, the myeloma cells which do not produce immunoglobulin light chains such as P3X63-Ag8.653, SP2/o-Ag14 and the like are preferably used. It is preferable that the antibody producing cells and the myeloma cells are derived from allogeneic, particularly syngeneic animals.

The method for preparing hybridomas by fusing antibody producing cells and myeloma cells may include a method using polyethylene glycol (PEG), a method using Sendai virus, a method using an electrofusion apparatus and the like. When PEG is used, spleen cells and myeloma cells are suspended at a mixing ratio of 1 to 10:1, preferably 5 to 10:1 in an appropriate medium or buffer containing about 30 to 60% of PEG (average molecular weight: 1000 to 6000) and incubated under the conditions of a temperature of about 25 to 37° C. and pH of 6 to 8 for about 30 seconds to 3 minutes. After the incubation, cells are washed to remove the PEG-containing solution, resuspended in a medium, seeded on a microtiterplate and cultured.

The thus fused cells are cultured on a selection medium to carry out selection of hybridomas. The selection medium may be the medium on which only fused cells can proliferate such as hypoxanthine-aminopterine-thymidine (HAT) medium. The selection of hybridomas can be generally carried out as follows: at 1 to 7 days after cell fusion, a part of, preferably about a half of the medium is exchanged to the selection medium, the cultivation is continued with the similar medium exchange at every 2 to 3 days and after completion of cultivation, wells in which hybridoma colonies are proliferated are selected under microscopic observation.

The thus obtained hybridomas may be confirmed whether or not they produce the desired antibody by carrying out the antibody titer assay on culture supernatant of the hybridomas. The antibody titer assay can be carried out according to the method known in the art. For example, the antibody can be detected by adding serial dilutions of the culture supernatant to an antigen protein immobilized on a solid phase and allowing reaction with a secondary antibody (anti-globulin antibody, anti-IgG antibody, anti-IgM antibody and the like) labeled with a fluorescent substance, enzyme or radioisotope (RI).

A single clone can be isolated from the hybridoma which is confirmed of its production of the desired antibody in the antibody titer assay by the limiting dilution analysis, the soft agar assay, a method using a fluorescence activated cell sorter and the like. In the limiting dilution analysis, for example, colonies of the hybridoma are serially diluted to around 1 cell/well in a medium before cultivation to isolate the hybridoma which produces the desired antibody.

The method for recovery of the monoclonal antibody from the hybridoma can be appropriately selected depending on the required amount of the monoclonal antibody or the properties of the hybridoma, which may include, for example, a method in which the monoclonal antibody is recovered from ascites of a mouse transplanted with the hybridoma, a method in which the monoclonal antibody is recovered from a cell culture supernatant and the like. The hybridoma which can proliferate intraperitoneally in mice can provide the monoclonal antibody with as high a concentration as several milligrams per ml of ascites. The hybridoma which can not proliferate in vivo can provide the monoclonal antibody from a cell culture supernatant. In this case, although the antibody production amount is low, purification is facilitated because of less contamination with immunoglobulins or other foreign substances.

When the antibody is obtained from the peritoneal cavity of a mouse transplanted with the hybridoma, a BALB/c mouse is preliminarily administered with an immunosuppressant such as pristane (2,6,10,14-tetramethyl pentadecane) and transplanted with the hybridoma (about $1 \times 10^6$ cells or more) before recovery of ascites after about 1 to 3 weeks. When heterogeneous hybridoma is transplanted, nude mice or radiation treated mice are preferably used.

When the antibody is obtained from a cell culture supernatant, the hybridoma may be cultivated, for example, by static culture which is used for cell maintenance as well as by a high density cultivation method or the spinner flask cultivation method and the culture supernatant containing the antibody can be obtained. It is preferable that the amount of serum in the medium is as low as possible because the addition of serum to the medium may cause contamination of foreign substances such as other antibodies and albumin to make purification of the antibody complicated. It is preferable that the hybridoma is adapted to a serum-free medium by the conventional method and is cultivated in the serum-free medium. This may facilitate the purification of the antibody.

The monoclonal antibody can be purified from ascites or a culture supernatant according to the method known in the art which may include, for example, the methods based on a fractionation method based on salt precipitation using salts such as ammonium sulfate, sodium sulfate and the like, a polyethylene glycol fractionation method, an ethanol fractionation method, DEAE ion-exchange chromatography, gel filtration chromatography and the like.

When the target antibody is murine IgG, the antibody can be purified with affinity chromatography using a Protein A-conjugated carrier or an anti-mouse immunoglobulin-conjugated carrier.

The first monoclonal antibody which is used for the present reagent includes, for example, an antibody (hereinafter also referred to as "FDP3-797 antibody") produced by a hybridoma "FDP3-797" which was deposited with Incorporated Administrative Agency National Institute of Technology and Evaluation Patent Microorganisms Depositary (2-5-8 Kazusakamatari, Kisarazu-shi, Chiba 292-0818 Japan) on Jun. 1, 2010 under the accession number of NITE BP-950.

The second monoclonal antibody which is used for the present reagent includes, for example, an antibody (hereinafter also referred to as "FDP3-2935 antibody") produced by a hybridoma "FDP3-2935" which was deposited with Incorporated Administrative Agency National Institute of Technology and Evaluation Patent Microorganisms Depositary (2-5-8 Kazusakamatari, Kisarazu-shi, Chiba 292-0818 Japan) on Jun. 1, 2010 under the accession number of NITE BP-951.

The third monoclonal antibody which is used for the present reagent includes, for example, an antibody (hereinafter also referred to as "DD-M1051 antibody") produced by a hybridoma "DD-M1051" which was deposited with Incorporated Administrative Agency National Institute of Technology and Evaluation Patent Microorganisms Depositary (2-5-8 Kazusakamatari, Kisarazu-shi, Chiba 292-0818 Japan) on Jun. 1, 2010 under the accession number of NITE BP-952.

The ratio of concentration between the respective monoclonal antibodies in the present reagent is not particularly limited and can be appropriately selected by a person skilled in the art.

The present reagent comprises a carrier sensitized with at least two monoclonal antibodies which have different reactivity towards FDP and are selected from the first, second and third monoclonal antibodies described hereinabove. The carrier may include organic polymeric compounds, inorganic compounds, erythrocytes and the like. The organic polymeric compounds may include insoluble agaroses, insoluble dextrans, celluloses, latexes, polystyrenes, styrene-methacrylic acid copolymers, styrene-glycidyl(meth)acrylate copolymers, styrene-styrene sulfonate copolymers, methacrylic acid polymers, acrylic acid polymers, acrylonitrile-butadiene-styrene copolymers, vinyl chloride-acrylic ester copolymers, poly(vinyl acetate-acrylates) and the like. The inorganic compounds may include silica, alumina and the like.

The shape of the carrier is not particularly limited and may be any shape of spherical, planar and the like. When the carrier is spherical, the average diameter of the carrier particles can be appropriately selected depending on measurement instruments and may appropriately be 0.05 to 0.5 μm in general. The material of the particles is particularly preferably latex.

The first, second and third monoclonal antibodies may be linked to the carrier according to any of physical adsorption and chemical binding methods known in the art, among which physical adsorption methods are preferred because the procedures are simple.

When the carrier is particles, the carrier particles may be carrier particles each being sensitized with two or three monoclonal antibodies, or may be a mixture of carrier particles respectively sensitized with each monoclonal antibody. When the first, second and third monoclonal antibodies have different sensitization conditions to a carrier particle, these antibodies preferably sensitize carrier particles separately.

When the carrier particles are latex particles, the carrier particles sensitized with the monoclonal antibodies are suspended in an appropriate buffer. The concentration of latex particles in the suspension is preferably 0.5 to 10 mg/ml and more preferably 0.75 to 5 mg/ml. The total concentration of the monoclonal antibodies in the suspension is preferably 10 to 100 μg/ml and more preferably 20 to 50 μg/ml.

The buffer may include the buffer which has a buffering action at pH 5 to 10 and preferably pH 6 to 9. Specifically, the buffer may include, for example, phosphate buffers, imidazole buffers, triethanolamine-hydrochloric acid, Good's buffers and the like. Good's buffers may include MES, Bis-Tris, ADA, PIPES, Bis-Tris-Propane, ACES, MOPS, MOPSO, BES, TES, HEPES, HEPPS, Tricine, Tris, Bicine, TAPS and the like buffers. Among these, MOPSO is preferred.

The buffer may further comprise additives such as protein stabilizers (e.g., BSA and the like), preservatives (e.g., sodium azide, phenylmethanesulfonyl fluoride and the like), pH modifiers, sensitizers (e.g., polyvinylpyrrolidone, polyanions, polyethylene glycols, polysaccharides and the like), inorganic salts (e.g., sodium chloride, calcium chloride and the like), background reducing agents (e.g., human anti-mouse antibody (HAMA) absorbing agents and the like).

An embodiment of the present reagent may include a reagent kit for the measurement of FDP (hereinafter also referred to as the present reagent kit). The present reagent kit comprises a first reagent containing a buffer and a second reagent containing a suspension of carrier particles sensitized with at least two monoclonal antibodies selected from the first, second and third monoclonal antibodies.

The present reagent kit is the reagent kit for detecting FDP in a biological sample based on immunoassay, for example, an assay (latex agglutination) in which latex particles sensitized with the above at least two monoclonal antibodies and FDP in the sample are reacted.

Examples of the first, second and third monoclonal antibodies which are used in the present reagent kit may include FDP3-797, FDP3-2935 and DD-M1051 antibodies, respectively.

The present reagent kit is of a two-reagent type consisting of the first and second reagents as described above. However, the present reagent kit may be of a one-reagent type consisting of one reagent. In view of the measurement accuracy, the reagent kit is preferably of a two-reagent type consisting of the first and second reagents. More preferably, the present reagent kit is in the form comprising the first reagent containing the buffer and the second reagent consisting of the reagent for the measurement of FDP of the present invention.

The buffer which may be used for the first reagent constituting the present reagent kit may include the same buffers which may be used for suspending the carrier particles in the present reagent. The first reagent may contain protein stabilizers, preservatives, pH modifiers, sensitizers, inorganic salts and the like as described above.

The method for the measurement of FDP of the present invention can be carried out with the reagent or reagent kit for the measurement of FDP of the present invention. As an embodiment of the method for measurement of FDP of the present invention, the method for measurement of FDP in a biological sample with the reagent kit for the measurement of FDP of the present invention is specifically described hereinbelow.

The first reagent containing the buffer and a biological sample are first mixed and incubated. The biological sample may include serum, plasma, urine and the like which are obtained from a subject. The first reagent and the biological sample may be mixed at a volume ratio of about 5:1 to 50:1. The incubation may be carried out for about 1 to 10 minutes.

The mixture of the first reagent and the biological sample is then added with the second reagent containing a suspension of carrier particles sensitized with at least two monoclonal antibodies selected from the first, second and third monoclonal antibodies. The mixture and the second reagent may be mixed at a volume ratio of about 1:0.05 to 1:1.5.

When the second reagent is added and mixed, FDP and the carrier particles in the second reagent are aggregated because of antigen-antibody reaction. The degree of the aggregation is measured as the amount of change in absorbance per minute. This measurement is preferably carried out on an optical instrument which can measure scattered light intensity, absorbance or transmitted light intensity. The measurement wavelength may be appropriately selected from the range of 300 to 2400 nm, preferably 300 to 1000 nm and more preferably 500 to 1000 nm.

The concentration and/or amount of FDP in the biological sample can be calculated from the measured amount of change in absorbance based on a calibration curve prepared by measurements of the FDP standard substance having known concentrations.

The present reagent kit may also be applied for a method in which the first and second reagents are mixed prior to addition of a biological sample to the mixture of these reagents and optical measurement of the degree of aggregation of carrier particles.

Examples of the first, second and third monoclonal antibodies which are used in the present method for measurement of FDP may include FDP3-797, FDP3-2935 and DD-M1051 antibodies, respectively.

Examples are described hereinbelow, which do not limit the present invention.

EXAMPLES

Test Example 1

Studies on Reactivity of Monoclonal Antibodies

The difference in reactivity of the first, second and third monoclonal antibodies, FDP3-797, FDP3-2935 and DD-M1051 antibodies, respectively, towards fibrin and fibrinogen degradation products was studied by ELISA as follows.

(1) Preparation of FDP
(1-1) Preparation of Fibrinogen Degradation Products (FbgDP)

To 241 mg (39.7 mg/ml) of fibrinogen (Sigma) was added plasmin (Sigma) to a final concentration of 60 mU/ml and incubated at 37° C. for 8 hours. Aprotinin was then added to a final concentration of 1 U/ml to terminate the degradation reaction. The obtained reaction solution was centrifuged at 12,000×g for 20 minutes, the obtained supernatant was subjected to chromatography on a lysine-Sepharose 4B column (volume: 8 ml) equilibrated with a 50 mM Tris buffer (pH 7.4) followed by removal of Sepharose on a spin column to prepare a FbgDP solution. The protein concentration of the obtained FbgDP solution was measured with a protein quantification reagent (Bio-Rad). A part of the FbgDP solution was used for evaluation of reactivity towards FDP of the reagent for the measurement of FDP of the present invention as described hereinbelow.

The obtained FbgDP solution was exchanged twice to a sample buffer (62.5 mM Tris, 192 mM glycine and 1% SDS (pH 6.8)) with an ultrafiltration centrifuge tube (Amicon 15 50K; Millipore). The obtained solution was charged into Sephacryl S-300 (GE Healthcare) at a flow rate of 70 to 80 μl/min with a peristaltic pump and fractions were collected every 10 minutes. The respective fractions obtained were analyzed on SDS-PAGE with molecular weight markers to recover the fractions respectively containing the fragment X, fragment Y and fragment D. The fractions were exchanged twice to a phosphate buffer (PBS) with Amicon 15 50K (Millipore) to obtain FbgDP antigens.

(1-2) Preparation of Fibrin Degradation Products (FbnDP)

To 92 mg (23 mg/ml) of fibrinogen (Sigma) were added calcium chloride, human thrombin (Mitsubishi Pharma Corporation) and factor XIII (Nipro) at final concentrations of 25 mM, 4 U/ml and 0.05 U/ml, respectively and incubated at 37° C. for overnight to convert fibrinogen to fibrin. The generated fibrin gel in the reaction solution was washed with 50 ml of Tris buffer (TBS (pH 7.4)) and centrifuged at 4° C., 3,000×g for 10 minutes to collect the fibrin gel. The same procedure was repeated twice followed by grinding the fibrin gel with a 50-ml syringe. The fibrin gel was resuspended in 4.6 ml of TBS (pH 7.4). The suspension was added with plasmin to a final concentration of 75 mU/ml and incubated at 37° C. for 6 hours. Aprotinin was then added to a final concentration of 1 U/ml to terminate the degradation reaction. The obtained reaction solution was centrifuged at 12,000×g for 20 minutes, the obtained supernatant was subjected to chromatography on a lysine-Sepharose 4B column (volume: 3.5 ml) equilibrated with a 50 mM Tris buffer (pH 7.4) followed by removal of Sepharose on a spin column to prepare a FbnDP solution. The protein concentration of the obtained FbnDP solution was measured with a protein quantification reagent (Bio-Rad). A part of the FbnDP solution was used for evaluation of reactivity towards FDP of the reagent for the measurement of FDP of the present invention as described hereinbelow.

The obtained FbnDP solution was exchanged three times to a sample buffer (62.5 mM Tris, 192 mM glycine and 1% SDS (pH 6.8)) with an ultrafiltration centrifuge tube (Amicon 15 50K; Millipore). The obtained solution was charged into Sephacryl S-300 (GE Healthcare) at a flow rate of 2 ml/min with a peristaltic pump and fractions were collected every 30 seconds. The respective fractions obtained were analyzed on SDS-PAGE with molecular weight markers to recover the fractions respectively containing the fragment XDP, fragment DD/E and fragment DD. The fractions were exchanged twice to a phosphate buffer (PBS) with Amicon 15 50K (Millipore) to obtain FbnDP antigens.

Respective anti-FDP monoclonal antibody solutions were diluted to 0.5 μg/ml in PBS, dispensed into the wells of 96-well microtiterplates at 100 μl/well and left to stand at 4° C. for 18 hours. The wells were washed three times with 10 mM phosphate buffer (pH 7.0) containing 0.05% Tween 20 (hereinafter referred to as the washing solution). The wells were then filled with 10 mM phosphate buffer containing 1% BSA (hereinafter referred to as the blocking buffer) to obtain antibody solid phases of anti-FDP monoclonal antibodies.

After the wells were again washed three times with the washing solution, the wells of antibody solid phases were added with 100 μl of the respective FbgDP antigens and FbnDP antigens prepared as described above and incubated at room temperature for 30 minutes. After the incubation, the wells were washed three times with the washing solution, respectively added with 100 μl of a peroxidase-labeled anti-fibrinogen antibody (DAKO) and incubated at room temperature for one hour. After the incubation, the wells were washed three times with the washing solution, respectively added with 100 μl of an ODP substrate solution (International Reagents Co., Ltd.) and incubated at room temperature for 15 minutes. The wells were then respectively added with 100 μl of 2N sulfuric acid to terminate the reaction and absorbance was measured at 490 nm.

The results are shown in Table 1.

TABLE 1

| | | FDP3-797 | FDP3-2935 | DD-M1051 |
|---|---|---|---|---|
| Primary fibrinolysis products | Fragment X | + | − | + |
| | Fragment Y | + | + | + |
| | Fragment D | − | − | − |
| Secondary fibrinolysis products | Fragment XDP | + | + | + |
| | Fragment DD/E | + | + | + |
| | Fragment DD | + | + | + |

In Table 1, "+" denotes that the antibody has reactivity with the fragment and "−" denotes that the antibody has no reactivity with the fragment.

Table 1 shows that the FDP3-797 and DD-M1051 antibodies do not react with the fragment D but react with the fragments XDP, DD/E, DD, X and Y. It is also found that the FDP3-2935 antibody does not react with the fragments X and D but reacts with the fragments XDP, DD/E, DD and Y.

Example 1

Preparation of Reagent and Reagent Kit for the Measurement of FDP (1) Production of the First Reagent Containing Buffer The reagents were mixed at the final concentrations shown in Table 2, adjusted to pH 7.1 with 1M sodium hydroxide aqueous solution and adjusted to 1 liter with ultrapure water to produce a buffer.

TABLE 2

| Reagents | Final conc. | Manufacturer |
| --- | --- | --- |
| MOPSO | 75.5 mM | Dojindo Laboratories |
| Sodium chloride | 225 mM | Manac Inc. |
| Sodium azide | 0.10% | Kishida Chemical Co., Ltd. |
| BSA | 0.5% | PROLIANT |
| Ultrapure water | q.s. | |

(2) Production of Reagent for the Measurement of FDP Containing Suspension of Carrier Particles Sensitized with Anti-FDP Monoclonal Antibodies (2-1) Sensitization of Latex Particles with FDP3-797 Antibody The FDP3-797 antibody was mixed with a 50 mM 2-hydroxy-3-morpholinopropanesulfonic acid/150 mM NaCl solution to a final concentration of 1 mg/ml. This mixture was mixed with a 20% (weight ratio) latex suspension (particle diameter: 0.238 µm; JSR Corporation).

The obtained mixture was mixed with an equivalent amount of a 50 mM 2-hydroxy-3-morpholinopropanesulfonic acid/150 mM NaCl/2% BSA solution, followed by centrifugation at 10° C., 38,400×g for 30 minutes. The supernatant was removed and the obtained precipitate was added with a 50 mM 2-hydroxy-3-morpholinopropanesulfonic acid/150 mM NaCl/2% BSA/1.5% sucrose solution at the amount equivalent to the supernatant.

The obtained mixture was subjected to sonication under ice-cold conditions on an ultrasonic grinder (Otake Seisakusho K.K.) and an ultrasonic processor (equivalent to UP-200S from Dr. Hielscher GmbH) to obtain a suspension of latex particles sensitized with the FDP3-797 antibody (antibody concentration: 39 µg/ml).

(2-2) Sensitization of Latex Particles with FDP3-2935 Antibody

The FDP3-2935 antibody was mixed with a 50 mM 2-hydroxy-3-morpholinopropanesulfonic acid/150 mM NaCl solution to a final concentration of 1 mg/ml. A suspension of latex particles sensitized with the FDP3-2935 antibody (antibody concentration: 39 µg/ml) was obtained in the same manner as described in the above "(2-1) Sensitization of latex particles with FDP3-797 antibody".

(2-3) Sensitization of Latex Particles with DD-M1051 Antibody

The DD-M1051 antibody was mixed with a 50 mM 2-hydroxy-3-morpholinopropanesulfonic acid/150 mM NaCl solution to a final concentration of 1 mg/ml. A suspension of latex particles sensitized with the DD-M1051 antibody (antibody concentration: 39 µg/ml) was obtained in the same manner as described in the above "(2-1) Sensitization of latex particles with FDP3-797 antibody".

(2-4) Production of Second Reagent

Figure 2:
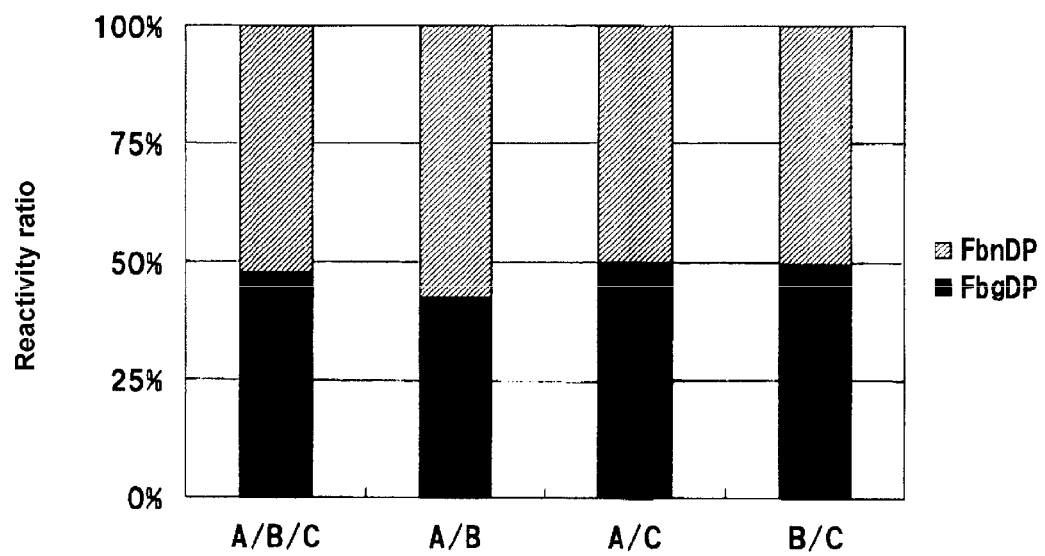
FIG. 2 is a graph showing the ratio of reactivity of the reagent for the measurement of FDP of the present invention towards primary and secondary fibrinolysis products.

In FIGS. 1 and 2 described below, the suspensions of latex particles sensitized with the FDP3-797, FDP3-2935 and DD-M1051 antibodies are respectively referred to as A, B and C. The reagents for the measurement of FDP containing carrier particles sensitized with two or three monoclonal antibodies were obtained by mixing equal amounts of these suspensions in the combinations of "A and B" (A/B in FIGS. 1 and 2), "A and C" (A/C in FIGS. 1 and 2), "B and C" (B/C in FIGS. 1 and 2), and "A, B and C" (A/B/C in FIGS. 1 and 2). These reagents for the measurement of FDP were hereinafter used as the second reagents.

Example 2

Confirmation of Reactivity of Reagents for the Measurement of FDP of the Present Invention Towards FDP in Latex Agglutination Method The ratio of reactivity of the reagents for the measurement of FDP produced in Example 1 towards fibrin degradation products and fibrinogen degradation products was evaluated according to the latex agglutination method following the procedures described below.

The FbgDP solution prepared in the above Test Example 1 was diluted in a TBS buffer to obtain a FbgDP specimen (protein concentration: 100 µg/ml). In the similar manner, a FbnDP specimen (protein concentration: 100 µg/ml) was prepared from the FbnDP solution.

An equivalent amount mixture of each 6 µl of FbgDP and FbnDP specimens was mixed with 84 µl of the first reagent prepared in the above Example 1 (1) and incubated at 37° C. for 20 seconds. The obtained reaction solution was mixed with 84 µl of the respective second reagents prepared in the above Example 1 (2) to initiate latex agglutination reaction. Absorbance at the wavelength of 800 nm at 1 minute and 2 minutes after the initiation of the reaction was measured with CS-2000i (Sysmex Corporation). From the measurement results, the amount of change in absorbance per minute was obtained. The ratio of reactivity was calculated from the reactivity towards FbgDP and that towards FbnDP. The results are shown in FIGS. 1 and 2.

The comparison, in FIG. 1, between the combination of FDP3-797 antibody/FDP3-2935 antibody (A/B in FIG. 1) and the combination of FDP3-2935 antibody/DD-M1051 antibody (B/C in FIG. 1) shows difference in the amount of change in absorbance, indicating that the FDP3-797 antibody and the DD-M1051 antibody have different reactivity towards FDP.

Thus, the reagents for the measurement of FDP obtained in the above Example 1 (2) are reagents comprising carrier particles sensitized with at least two monoclonal antibodies having different reactivity towards FDP.

FIG. 2 shows that all reagents of any antibody combinations had almost uniform reactivity towards FbgDP and FbnDP. Therefore, it is demonstrated that the reagent and reagent kit for the measurement of FDP of the present invention can measure FDP with high accuracy even in biological samples containing primary fibrinolysis products.

Example 3

Comparison Between Reagent Kit for the Measurement of FDP of the Present Invention and Other Company Products The reagent kit for the measurement of FDP of the present invention obtained in the above Example 1 and other company products were used to measure FDP.

The first reagent of the reagent kit for the measurement of FDP of the present invention was the reagent prepared in the above Example 1 (1). The second reagent was the reagent containing the suspension of latex particles which were respectively sensitized with three antibodies, which was prepared in the above Example 1 (2). The specimen (FDP sample) used was an equivalent amount mixture of the FbgDP specimen and the FbnDP specimen used in the above Example 2.

The specimen (6 μl) was mixed with 84 μl of the first reagent and incubated at 37° C. for 20 seconds. The obtained reaction solution was mixed with 84 μl of the second reagent to initiate latex agglutination reaction. For other company products A to C, reagents were similarly mixed with the panel of plasma according to the instructions attached to these products to initiate latex agglutination reaction. Absorbance at the wavelength of 800 nm at 1 minute and 2 minutes after the initiation of the reaction was measured with CS-2000i. From the measurement results, the amount of change in absorbance per minute was obtained for each group. The ratio of reactivity was calculated from the reactivity towards FbgDP and that towards FbnDP. The results are shown in FIG. 3.

Figure 3:
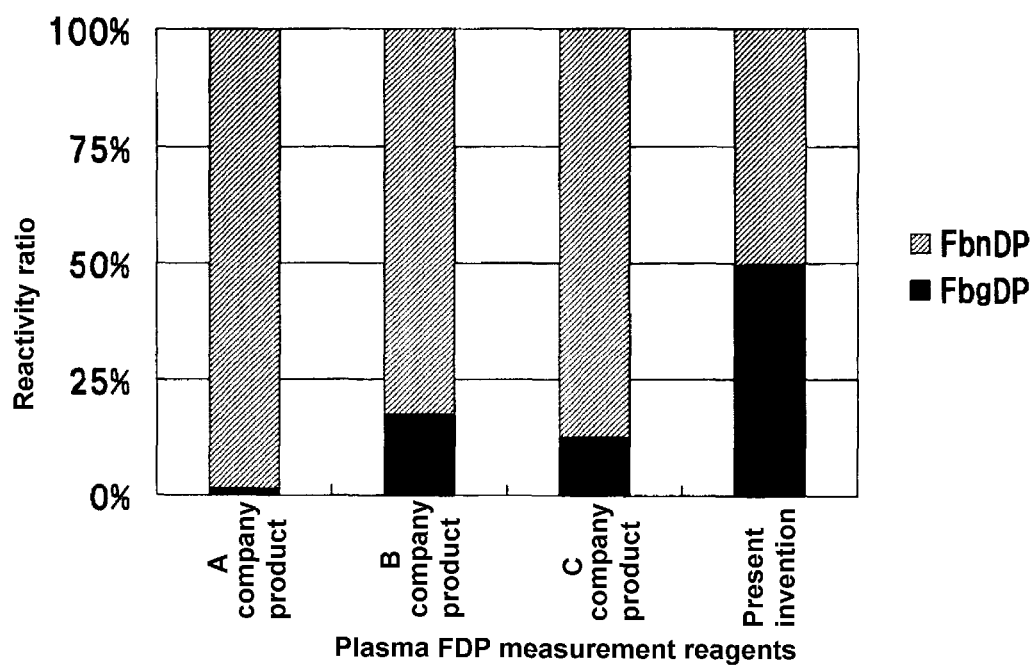
FIG. 3 is a graph showing difference between the ratio of reactivity of the reagent for the measurement of FDP of the present invention and that of other company products towards primary and secondary fibrinolysis products.

FIG. 3 shows that the reagent for the measurement of FDP of the present invention reacted equally towards FbgDP and FbnDP while other company products showed stronger reactivity towards FbnDP than towards FbgDP.

Therefore, it is demonstrated that the reagent and reagent kit for the measurement of FDP of the present invention can measure with higher accuracy the FDP concentration even in biological samples containing primary fibrinolysis products than other company products.

What is claimed is:

1. A reagent for the measurement of Fibrin Degradation Products (FDP) comprising at least two monoclonal antibodies which have different reactivity towards FDP and are selected from the group consisting of:
   a first monoclonal antibody produced by the hybridoma deposited with Incorporated Administrative Agency National Institute of Technology and Evaluation Patent Microorganisms Depositary on Jun. 1, 2010 under the accession number of NITE BP-950;
   a second monoclonal antibody produced by the hybridoma deposited with Incorporated Administrative Agency National Institute of Technology and Evaluation Patent Microorganisms Depositary on Jun. 1, 2010 under the accession number of NITE BP-951; and
   a third monoclonal antibody produced by the hybridoma deposited with Incorporated Administrative Agency National Institute of Technology and Evaluation Patent Microorganisms Depositary on Jun. 1, 2010 under the accession number of NITE BP-952.

2. The reagent for the measurement of FDP of claim 1, wherein the reagent further comprises carrier particles and the carrier particles are a mixture of carrier particles respectively sensitized with each monoclonal antibody.

3. The reagent of claim 1, wherein the reagent comprises at least the first monoclonal antibody and the second monoclonal antibody.

4. The reagent of claim 1, wherein the reagent comprises at least the first monoclonal antibody and the third monoclonal antibody.

5. The reagent of claim 1, wherein the reagent comprises at least the second monoclonal antibody and the third monoclonal antibody.

6. A reagent kit for the measurement of Fibrin Degradation Product (FDP) comprising:
   a buffer; and
   the reagent of claim 1.

7. The reagent kit of claim 6, wherein the reagent further comprises carrier particles and the carrier particles are a mixture of carrier particles respectively sensitized with the first, the second and the third monoclonal antibodies.

8. The reagent kit of claim 6, wherein the reagent comprises at least the first monoclonal antibody and the second monoclonal antibody.

9. The reagent kit of claim 6, wherein the reagent comprises at least the first monoclonal antibody and the third monoclonal antibody.

10. The reagent kit of claim 6, wherein the reagent comprises at least the second monoclonal antibody and the third monoclonal antibody.

11. A method for measuring FDP comprising the steps of:
    obtaining a biological sample;
    mixing said biological sample with the reagent of claim 1; and
    measuring aggregation, thereby detecting FDP.

12. The method of claim 11, wherein the measuring step involves measuring a change in absorbance.

* * * * *